(12) United States Patent
Usala (10) Patent No.: US 6,352,707 B1
(45) Date of Patent: *Mar. 5, 2002

(54) TRANSPLANT ENCAPSULATION IN A HYDROGEL MATRIX TO OBSCURE IMMUNE RECOGNITION

(76) Inventor: Anton-Lewis Usala, 237 Buckingham Dr., Winterville, NC (US) 28590

( * ) Notice: Subject to any disclaimer, the term of this patent is extended or adjusted under 35 U.S.C. 154(b) by 0 days.

This patent is subject to a terminal disclaimer.

(21) Appl. No.: 09/346,212

(22) Filed: Jul. 1, 1999

Related U.S. Application Data (63) Continuation-in-part of application No. 09/113,437, filed on Jul. 10, 1998, now Pat. No. 6,231,881, which is a continuation of application No. 08/568,482, filed on Dec. 7, 1995, now Pat. No. 5,834,005, which is a continuation-in-part of application No. 08/300,429, filed on Sep. 2, 1994, now abandoned, which is a continuation-in-part of application No. 07/841,973, filed on Feb. 24, 1992, now abandoned.

(51) Int. Cl.⁷ ............................ A61F 2/00; C12N 11/02; C12N 11/10; C12N 5/06; C12N 5/08
(52) U.S. Cl. ...................... 424/423; 424/93.7; 435/177; 435/178; 435/182; 435/382; 435/395; 435/397
(58) Field of Search ................................ 434/177, 178, 434/182, 382, 395, 397; 424/423, 93.7

(56) References Cited

U.S. PATENT DOCUMENTS

| | | |
|---|---|---|
| 4,198,479 A | 4/1980 | Tytell et al. |
| 4,477,567 A | 10/1984 | Healy et al. |
| 4,520,821 A | 6/1985 | Schmidt et al. |
| 4,657,866 A | 4/1987 | Kumar ........................ 435/240 |
| 4,863,856 A | 9/1989 | Dean, Jr. et al. |
| 4,902,295 A | 2/1990 | Walthall et al. |
| 4,950,483 A | 8/1990 | Ksander et al. ............. 424/422 |
| 4,978,616 A | 12/1990 | Dean, Jr. et al. |
| 4,997,753 A | 3/1991 | Dean, Jr. et al. |
| 5,021,349 A | 6/1991 | Drouet et al. |
| 5,100,783 A | 3/1992 | Dean, Jr. et al. |
| 5,116,753 A | 5/1992 | Beattie et al. |
| 5,132,223 A | 7/1992 | Levine et al. |
| 5,405,772 A | 4/1995 | Ponting |
| 5,605,938 A | 2/1997 | Roufa et al. ................... 514/59 |
| 5,645,591 A | 7/1997 | Kuberasampath et al. .... 623/16 |
| 5,672,361 A | 9/1997 | Halberstadt et al. |
| 5,681,587 A | 10/1997 | Halberstadt et al. |
| 5,716,404 A | 2/1998 | Vacanti et al. |
| 5,824,331 A | 10/1998 | Usala ........................ 424/424 |
| 5,830,492 A | 11/1998 | Usala ........................ 424/424 |
| 5,834,005 A | 11/1998 | Usala ........................ 424/424 |
| 5,840,059 A | 11/1998 | March et al. ................. 604/53 |
| 5,855,617 A | 1/1999 | Orton ........................ 623/11 |

FOREIGN PATENT DOCUMENTS

| | | |
|---|---|---|
| DE | 4431598 A1 | 3/1996 |
| EP | 0 213 908 A2 | 3/1987 |
| EP | 03 363 125 A2 | 10/1989 |
| EP | 0 481 791 A2 | 4/1992 |
| EP | 0 526 756 A | 2/1993 |
| EP | 0 564 786 A | 10/1993 |
| WO | 98/04681 | 2/1988 |
| WO | 91/09119 A2 | 12/1991 |
| WO | 92/19195 A1 | 11/1992 |
| WO | 93/00441 | 1/1993 |
| WO | 93/24112 A1 | 12/1993 |
| WO | 94/03154 A1 | 2/1994 |
| WO | 94 08702 | 4/1994 |
| WO | 94/15589 A1 | 12/1994 |
| WO | 95/14037 | 5/1995 |
| WO | 95/29231 | 11/1995 |
| WO | 97 20569 A | 6/1997 |
| WO | 97 39107 | 10/1997 |
| WO | 98/16629 | 4/1998 |

OTHER PUBLICATIONS

Donofrio, "The Effects of Growth Factors on Proliferation of Adult Porcine Islets In Vitro", Department of Biology, East carolina University (May 1997).

Hubbell, et al., "Tissue Engineering," Chemical & Engineering News, (Mar. 13, 1995), pp. 42–54.

Metrakos, et al., "Collagen Gel Matrix Promotes Islet Cell Proliferation", Transplantation Proceedings, vol. 26, No. 6 (Dec. 1994) pp. 3349–3350.

Mandel et al., "Organ Culture of Fetal Mouse and Fetal Human Pancreatic Islets for Allograftting," Diabetes, vol. Suppl. 4 (Aug. 1982), pp. 39–47.

Isner, et al., "Therapeutic Angiogensis", Frontiers in Bioscience, vol. 3 (May 5, 1998) pp. 49–69.

*Primary Examiner*—David M. Naff
(74) *Attorney, Agent, or Firm*—Alston & Bird LLP (57) ABSTRACT

Immune recognition of a transplant such as tissue implanted in a host mammal is obscured by encapsulating the transplant in a hydrogel matrix containing gelatin, dextran, at least one nitric oxide inhibitor and polar amino acids. The polar amino acids increase rigidity of the matrix and allow direct injection of the encapsulated transplant into a mammal without further immunosuppression. Preferably, the nitric oxide inhibitor is a combination of L-cysteine and an L-arginine analogue such as aminoguanidine, and the polar amino acids are a combination of L-glutamic acid, L-lysine and L-arginine. The matrix may also contain a superoxide inhibitor such as EDTA. Implanting can be carried out by applying a buffer medium containing a nitric oxide inhibitor to an implant site, implanting the encapsulated transplant, and applying to the implant site a buffer medium which may contain a nitric oxide inhibitor. The buffer medium may also contain a superoxide inhibitor. The buffer medium applied after implanting, may be applied once a day for about one to about seven days. The matrix binds to cell surface proteins of encapsulated transplant tissue to obscure recognition of the tissue by antibodies produced by a recipient of the tissue.

29 Claims, 3 Drawing Sheets

TRANSPLANT ENCAPSULATION IN A HYDROGEL MATRIX TO OBSCURE IMMUNE RECOGNITION

CROSS-REFERENCE TO RELATED APPLICATIONS

This application is a continuation-in-part of application Ser. No. 09/113,437, filed Jul. 10, 1998, now U.S. Pat. No. 6,231,881, which is a continuation of application Ser. No. 08/568,482, filed Dec. 7, 1995, now U.S. Pat. No. 5,834,005, which is a continuation-in-part of application Ser. No. 08/300,429, filed Sep. 2, 1994, now abandoned, which is a continuation-in-part of application Ser. No. 07/841,973, filed Feb. 24, 1992, now abandoned, which are incorporated herein by reference.

FIELD OF INVENTION

The present invention is drawn to methods and compositions for obscuring immune recognition in a mammal. More particularly, the present invention is drawn to methods of encapsulating tissue within a hydrogel matrix.

BACKGROUND OF THE INVENTION

The body defends itself from infectious agents through an immune response. Broadly speaking, the body has many layers of defense, including physical barriers like the skin, protective chemical substances, the blood and tissue fluids, and the physiologic reactions of tissues to injury or infection. The most effective defense strategy, however, is carried out by cells that have evolved specialized abilities to recognize and eliminate potentially injurious substances.

The response of a body to an infection occurs in the form of inflammation. An inflammatory response involves the passage of fluids, proteins, and cells from the blood into focal areas and tissues. The result is the local delivery of agents that can effectively combat infections. The process involves inflammatory cells, products of inflammatory cells, blood proteins, and pathways of response. Initiation of an inflammatory response begins by an increase in blood flow to infected tissues and by the separation of cells lining the blood vessels or capillaries, followed by emigration of cells into the involved tissue.

The immune response involves both humoral and cellular immune responses. Both responses are essential components of the defense against pathogenic bacteria, viruses, parasites, and other foreign objects. Cellular immunity is mediated by a class of white blood cells called lymphocytes. These cells originate from stem cells in the bone marrow and migrate to the thymus gland. While in the thymus, they undergo differentiation before emigrating to the peripheral lymphoid organs. Cells processed in the thymus are referred to as T-lymphocytes or T-cells. T-cells can destroy cells infected by various types of viruses or intracellular bacteria. Humoral immunity, or the humoral response, is mediated by antibodies. Antibodies are protein molecule synthesized by another class of lymphocyte called B-cells. B-cells also originate from stem cells in the bone marrow, but do not enter the thymus. B-cells are found in all peripheral lymphoid organs, and the antibodies they secrete are found throughout the body. The immune response is a complex intricately regulated sequence of events involving these cell types. It is triggered when an antigen, or foreign object, enters the body.

Among the major obstacles in research directed to pancreatic islet transplantation for the treatment of diabetes is an inability to induce permissive acceptance of xenograft tissue transplants in the host mammal. Current methods of transplantation must suppress immune response by the host mammal that may lead to rejection of the transplanted cells and loss of islet function. Many transplantation approaches require the host to take general immunosuppressive agents to prevent a host immune response from destroying the transplanted tissue. However, such immunosuppressive agents are undesirable because they reduce the immune response of the host generally, and thus can lead to poor health. Thus, there is also a need in the art for a simple, non-invasive method of introducing a transplant into a host without requiring general immunosuppressive agents.

SUMMARY OF THE INVENTION

The present invention provides a method of obscuring immune recognition of a transplant by encapsulating the tissue of the transplant within a hydrogel matrix comprising highly polar amino acids and gelatin fragments, such as denatured collagen fragments, having exposed polar groups. The exposed polar groups of the collagen fragments and the polar amino acids enable the matrix to bind to cell surface proteins, thereby obscuring the cell surface proteins, particularly from specific high affinity antibodies of the host organism. Since the high affinity antibodies are unable to recognize the protein structure of the foreign tissue, the antibodies are unable to stimulate immune response and destroy the transplant. The methods and compositions of the present invention are even effective in obscuring immune recognition of xenograft transplants, such that permissive acceptance of the xenograft transplant by the host organism is achieved.

In particular, the present invention provides a method of obscuring immune recognition of a transplant by a host mammal. The method includes providing tissue for suitable use in the transplant, wherein the tissue comprises cells having cell surface proteins. The tissue is encapsulated in the hydrogel matrix to form a transplant, wherein the matrix binds to the cell surface proteins of the encapsulated tissue. Thereafter, the thus-formed transplant may be implanted into a transplant site in a mammal. For example, the transplant may be implanted intramuscularly, subcutaneously, intra-organ, intravascularly, or in the peritoneal cavity.

In some embodiments, the transplant site may be prepared prior to implanting the above-described transplant by applying a buffer medium to the transplant site, wherein the buffer medium comprises at least one nitric oxide inhibitor, such as L-cysteine and aminoguanidine. For example, the applying step may comprise injecting about 10 to about 300 cc of the buffer medium into the transplant site prior to implantation. Periodically, after implantation of the transplant, further applications of the buffer medium to the transplant site may be made.

BRIEF DESCRIPTION OF THE DRAWINGS

Having thus described the invention in general terms, reference will now be made to the accompanying drawings, wherein:

DETAILED DESCRIPTION OF THE INVENTION

The invention comprises compositions and methods useful for making and using transplants. The invention also comprises compositions and methods of maintaining cell viability and function within a transplant over long periods of time. Specifically, the invention provides a method of obscuring immune recognition of a transplant and inducing permissive acceptance of the transplant by a host mammal. The present invention can be utilized to administer transplants to any mammal in need thereof. Mammals of interest include humans, dogs, cows, pigs, cats, sheep, horses, and the like, preferably humans.

By transplant is intended cells, tissues, or other living or non-living devices for transplantation into a mammal. Transplants of the invention include xenografts, allografts, artificial organs, cellular transplantation and other applications for hormone producing or tissue producing implantation into deficient individuals who suffer from conditions such as diabetes, thyroid deficiency, growth hormone deficiency, congenital adrenal hyperplasia, Parkinson's disease, and the like. Likewise, the method of the present invention is useful for transplants involving therapeutic conditions benefiting from implantable delivery systems for biologically active and gene therapy products for the treatment of central nervous system diseases and other chronic disorders. More specifically, the method as described will find application in the various transplantation therapies, including without limitation, cells secreting insulin for treatment of diabetes, cells secreting human nerve growth factors for preventing the loss of degenerating cholinergic neurons, satellite cells for myocardial regeneration, striatal brain tissue for Huntington's disease, liver cells, bone marrow cells, dopamine-rich brain tissue and cells for Parkinson's disease, cholinergic-rich nervous system for Alzheimer's disease, adrenal chromaffin cells for delivering analgesics to the central nervous system, cultured epithelium for skin grafts, and cells releasing ciliary neurotropic factor for amyotrophic lateral sclerosis, and the like. Examples of cells that may be suitable for inclusion in a transplant include cells derived from a variety of tissues such as lung, liver, kidney, thymus, thyroid, heart, brain, pancreas (including acinar and islet cells), and the like, as well as various cultured cell populations.

In the present invention, immune recognition of the transplant by the host mammal is obscured by encapsulating the transplant within a hydrogel matrix. The hydrogel matrix includes a gelatin component having exposed polar groups. For example, the exposed polar groups may be amine and carbonyl groups. The gelatin component provides scaffolding for cellular attachment. The preferred gelatin component is denatured collagen. Denatured collagen contains polar and non-polar amino acids that readily form a gel based on amine, carboxyl group, hydroxyl group, and sulfhydryl group interactions.

The gelatin is present at a concentration of about 0.01 to about 40 mM, preferably about 0.05 to about 30 mM, most preferably about 1 to 5 mM. Advantageously, the gelatin concentration is approximately 1.6 mM. The above concentrations provide a solid phase at storage temperature and a liquid phase at transplant temperature. In order to increase cell binding, intact collagen may be added in small amounts to provide an additional binding network for the cells contained in the matrix. The final concentration of intact collagen is from about 0 to about 5 mM, preferably 0 to about 2 mM, most preferably about 0.05 to about 0.5 mM. In one embodiment, the concentration of intact collagen is about 0.11 mM.

The gelatin component of the matrix of the present invention is mixed with a liquid composition. The liquid composition is preferably based upon a standard culture medium, such as Medium 199, supplemented with additives as described below.

Dextran is loosely polymerized around the gelatin component and facilitates cell attachment by preventing movement of the scaffolding provided by the gelatin. For tissue-containing transplants, this allows the cells within the tissue of the transplant to firmly attach to the matrix. Dextran is present at a concentration of about 0 to about 2 mM, preferably 0 to about 1 mM, most preferably about 0 to about 0.1 mM. In one embodiment, dextran is present in a concentration of about 0.086 mM.

The matrix also includes an effective amount of polar amino acids, such as arginine, lysine, histidine, glutamic acid, and aspartic acid, which further enhance the bioadhesiveness of the matrix. An effective amount is the amount necessary to increase the rigidity of the matrix and allow direct injection of the matrix with the transplant encapsulated therein into a host mammal without the need for further immunosuppression. In one embodiment, the concentration of polar amino acids is about 3 to about 150 mM, preferably about 10 to about 65 mM, and more preferably about 15 to about 40 mM.

Advantageously, the added polar amino acids comprise L-glutamic acid, L-lysine, and L-arginine. The final concentration of L-glutamic acid is about 2 to about 60 mM, preferably about 5 to about 40 mM, most preferably about 10 to about 20 mM. In one embodiment, the concentration of L-glutamic acid is about 15 mM. The final concentration of L-lysine is about 0.5 to about 30 mM, preferably about 1 to about 15 mM, most preferably about 1 to about 10 mM. In one embodiment, the concentration of L-lysine is about 5.0 mM. The final concentration of L-arginine is about 1 to about 40 mM, preferably about 1 to about 30, most preferably about 5 to about 15 mM. In one embodiment, the final concentration of L-arginine is about 10 mM.

Additionally, the matrix contains at least one nitric oxide inhibitor. Nitric oxide inhibitor is broadly defined as including any composition or agent that inhibits the production of nitric oxide or scavenges or removes existing nitric oxide. Nitric oxide is a pleiotropic mediator of inflammation. Nitric oxide is a soluble gas produced by endothelial cells, macrophages, and specific neurons in the brain, and is active in inducing an inflammatory response. Nitric oxide and its metabolites are known to cause cellular death from nuclear destruction and related injuries. Preferred nitric oxide inhibitors include L-cysteine, L-arginine analogues, cystine, and heparin.

Preferably, the matrix contains L-cysteine. L-cysteine acts as a nitric oxide scavenger and obscures immune recognition sites on the surface of cells. L-cysteine also provides disulfide linkages, which increases the matrix's resistance to force and further protects the cells contained therein. The final concentration of L-cysteine is about 5 to about 500 $\mu$M, preferably about 10 to about 100 $\mu$M, most preferably about 15 to about 25 $\mu$M. In one embodiment, the final concentration is about 20 $\mu$M.

Advantageously, aminoguanidine is also added to the matrix of the present invention. As indicated above, aminoguanidine is an L-arginine analogue and acts as a nitric oxide inhibitor. Other L-arginine analogues could also be used in the present invention. The final concentration of aminoguanidine is about 5 to about 500 $\mu$M, preferably about 10 to about 100 $\mu$M, most preferably about 15 to about 25 $\mu$M. In one embodiment, the final concentration is about 20 $\mu$M.

Additionally, the matrix of the present invention may include a superoxide inhibitor. A preferred superoxide inhibitor is ethylenediaminetetraacetic acid (EDTA). Superoxide is a highly toxic reactive oxygen species, whose formation is catalyzed by divalent transition metals, such as iron, manganese, cobalt, and sometimes calcium. Highly reactive oxygen species such as superoxide ($O_2^-$) can be further converted to the highly toxic hydroxyl radical ($OH^-$) in the presence of iron. By chelating these metal catalysts, EDTA serves as an antioxidant. EDTA is also a divalent cation chelator, which increases the rigidity of the matrix by removing inhibition of —$NH_2$ to —COOH hydrogen bonding. The concentration range for the superoxide inhibitor is about 0 to about 10 mM, preferably 1 to about 8 mM, most preferably about 2 to about 6 mM. In a preferred embodiment, the superoxide inhibitor is present at a concentration of about 4 mM.

Other additives known in the art may be included in the matrix. For example, although serum is not required, albumin or other nutrient sources may be added. If used, the albumin is preferably derived from the same species as the cells to be encapsulated within the matrix.

Table 1 below lists particularly preferred components of the matrix of the present invention along with suitable concentrations as well as preferred concentrations for each component.

TABLE 1

| Component | Concentration Range | Preferred Concentration |
| --- | --- | --- |
| L-glutamic acid | 2 to 60 mM | 15 mM |
| L-lysine | .5 to 30 mM | 5.0 mM |
| L-Arginine | 1 to 40 | 10 mM |
| Gelatin | 0.01 to 40 mM | 1.6 mM |
| L-cysteine | 5 to 500 µM | 20 µM |
| Aminoguanidine | 5 to 500 µM | 20 µM |
| Intact collagen | 0 to 5 mM | 0.11 mM |
| EDTA | 0 to 10 mM | 4 mM |
| Albumin | 0 to 2% by volume | 0.05% by volume |
| Dextran | 0 t0 2 mM | 0.086 mM |

Although the present invention is not bound by any particular theory, it is believed that the exposed polar groups of the gelatin component of the matrix, enhanced by the addition of highly polar amino acids, allow the gelatin fragments, such as denatured collagen fragments, to dock or bind to cell surface proteins of the cells of the transplant. By binding to the cell surface proteins, the matrix prevents specific high affinity antibodies from recognizing the specific protein structure of the transplanted tissue and binding to the tissue. This avoids the cascade of cytotoxic pathways that may lead to destruction of the transplanted tissue. Instead, less specific lower affinity antibodies are formed which do not stimulate the same cascade of cytotoxic pathways. These lower affinity antibodies are apparently able to bind to the transplanted tissue; thereby further protecting the cells within the transplant from high affinity/high kill antibody destruction.

The present invention is capable of protecting autologous, allogeneic and xenogeneic tissue from the immune response of a host mammal. Autologous refers to tissue that is derived from the transplant recipient. Allogeneic or allograft refers to tissue that is derived from the same species as the recipient. Xenogeneic and xenograft refers to tissue that is derived from a species other than that of the recipient. Using the methods of the present invention, isolated tissue from one species may be implanted in an animal of a different species without provoking a destructive immune response and without the need for general immunosuppressive agents. However, the methods of the present invention may be utilized in combination with other immune suppression methods or compositions known in the art.

For example, as described in copending U.S. application Ser. No. 09/113,437, which is herein incorporated by reference in its entirety, porcine pancreatic tissue, including both islet tissue and acinar tissue, may be encapsulated in the above-described hydrogel matrix and implanted into a diabetic mammal, thus providing in vivo insulin production. Similarly, other tissues that produce finctional products may be utilized in the present invention to provide replacement therapy for specific moieties for extended periods of time without the use of general immunosuppressive agents.

The transplant may be encapsulated by surrounding the transplant with the matrix using any conventional technique known in the art. For example, if the transplant comprises tissue, the tissue may be encapsulated within the matrix by adding a volume of the matrix to the tissue prior to implanting the tissue. If the transplant is a device that will be surgically implanted, the transplant may be encapsulated by applying the matrix to the transplant site before and/or after implantation of the transplant in order to surround the transplant with the matrix.

The encapsulated transplant may be implanted using any conventional method known in the art. For example, encapsulated tissue may be placed within a coated carrier device such as described in U.S. Pat. No. 5,824,331, which is herein incorporated by reference in its entirety, and surgically implanted. A carrier device includes any device designed to contain and protect tissue transplanted into a host organism. Examples of other transplant devices suitable for use with the matrix include those described in U.S. Pat. Nos. 5,686,091, 5,676,943 and 5,550,050.

However, the matrix may be used as the sole transplant vehicle without using such devices. In this manner, tissue may be encapsulated within the matrix and directly implanted into a host mammal without use of an additional protective carrier device. The tissue encapsulated within the matrix may be directly implanted by injection or any other suitable means known in the art.

The encapsulated transplant is implanted into a predetermined transplant site. A transplant site is broadly defined as any site within the host mammal wherein a transplant may be placed, including intramuscularly, subcutaneously, intraorgan, intravascularly, or in the peritoneal cavity.

The amount of encapsulated tissue injected or otherwise administered to the host depends on numerous factors, including the size and weight of the recipient, the nature and type of tissue, and the like. In one embodiment, for an intramuscular injection, the tissue/matrix is directly injected into a muscle with a maximum volume of about 0.75 ml/kg body weight per site, up to a total body load of 10 ml/kg body weight. In another embodiment, for an intraperitoneal injection, the recipient is lightly anesthetized, and a 14–18 gauge catheter is inserted into the peritoneal cavity for administering the tissue/matrix to the recipient. Preferably, the intraperitoneal injection comprises about 0.1 to about 500 ml. of the tissue/matrix transplant.

In one embodiment, the transplant site is prepared by applying an effective amount of the above-described matrix to the site prior to implantation of the transplant. The matrix can prepare the site by contributing to transplant site vascularization and nitric oxide inhibition.

In a preferred embodiment, the transplant site is prepared for implant by administering, such as by injection, a buffer medium, wherein the buffer medium comprises at least one nitric oxide inhibitor. The buffer medium is a solution containing growth factors and nutrients which are used to support the growth and development of cells. The buffer medium preferably comprises a standard culture medium supplemented with a buffering agent, salt solution and other additives, including a nitric oxide inhibitor.

The preferred standard culture medium is Medium 199 1×liquid. However, other standard culture media known in the art would be suitable for use with the present invention. Standard culture media which may be employed in accordance with the present invention are standard culture media for growing cells that typically provide an energy source, such as glucose, substantially all essential and nonessential amino acids and vitamins and/or other cell growth supporting organic compounds required at low concentrations. When combined with a buffering agent and a salt solution, the standard culture medium provides many of the nutrients required for normal metabolic functioning of cultured cells. The preferred salt solution is Earle's Balanced Salts. The salt solution helps to maintain pH and osmotic pressure and also provides a source of energy. The preferred buffering agent is Hepes. Other salt solutions and buffering agents known in the art may be used without departing from the present invention.

Suitable nitric oxide inhibitors for the buffer medium include L-cysteine, L-arginine analogues, cystine, and heparin. Aminoguanidine is a preferred L-arginine analogue. Other L-arginine analogues, such as N-monomethyl L-arginine, N-nitro-L-arginine or D-arginine could also be used in the present invention. In a preferred embodiment, aminoguanidine is provided at a concentration of about 15 to about 250 $\mu$M, preferably about 30 to 180 $\mu$M, most preferably about 80 to about 120 $\mu$M. In one embodiment, the concentration of aminoguanidine is about 100 $\mu$M.

The buffer medium also preferably includes L-cysteine. L-cysteine acts as a scavenger of already formed nitric oxide and thereby prevents nitric oxide induced cellular damage. Additionally, L-cysteine may obscure immune recognition sites on the cultured cells by sulfhydryl bond formation to integral surface proteins containing sulfur groups. Further, L-cysteine provides sulfhydryl bonds which strengthen cell membranes. The preferred final concentration of L-cysteine is about 50 to about 300 $\mu$M, preferably about 80 to about 250 $\mu$M, most preferably about 150 to about 200 $\mu$M. In one embodiment, the final concentration is about 180 $\mu$M.

The buffer medium may also include an effective amount of polar amino acids. The preferred polar amino acids are selected from the group consisting of arginine, lysine, histidine, glutamic acid, and aspartic acid, although other chemicals containing polar amine and carboxyl groups may be used. An effective amount is the amount necessary to strengthen cellular membranes and bond to immune recognition sites on the cell surface. In one embodiment, the concentration of polar amino acids is raised to a final concentration of between about 5 to about 150 mM, preferably about 10 to about 65 mM, and more preferably about 15 to about 40 mM. Advantageously, supplemental amounts of L-arginine and L-glutamic acid are added to the buffer medium. Preferably, the final concentration of L-arginine is about 2 to about 60 mM, preferably about 5 to about 30 mM, most preferably about 5 to about 15 mM. The final concentration of L-glutamic acid is about 2 to about 60 mM, preferably about 5 to about 30 mM, most preferably about 10 to about 20 mM. In one embodiment, the final concentration of L-arginine is about 10 mM and the final concentration of L-glutamic acid is about 15 mM.

Additionally, the buffer medium may include a superoxide inhibitor. A preferred superoxide inhibitor is ethylenediaminetetraacetic acid (EDTA). The concentration range for the superoxide inhibitor is about 0 to about 10 mM, preferably 1 to about 8 mM, most preferably about 2 to about 6 mM. In a preferred embodiment, the superoxide inhibitor is present at a concentration of about 4 mM.

Other additives known in the art, such as antibiotics, may be added to the buffer medium without departing from the present invention.

Table 2 below lists the particularly preferred additives and supplemental ingredients for the buffer medium of the present invention and summarizes the final concentration ranges and preferred final concentrations for each ingredient.

TABLE 2

| Components | Concentration Range | Preferred Concentration |
|---|---|---|
| Albumin | 5–50 $\mu$l/ml | 20 $\mu$l/ml |
| L-Cysteine HCl | 50–300 $\mu$M | 180 $\mu$M |
| Aminoguanidine | 15–250 $\mu$M | 100 $\mu$M |
| Coly-Mycin | 5–20 $\mu$g/ml | 10 $\mu$g/ml |
| Arnphotericin B | 2–6 $\mu$M | 3.382 $\mu$M |
| Ciprofloxacin | 2–6 $\mu$g/ml | 5 $\mu$g/ml |
| Gentamicin Sulfate | 2–6 $\mu$g/ml | 4.8 $\mu$g/ml |
| L-Glutamine | 5–15 $\mu$M | 10 $\mu$M |
| L-Glutamic Acid | 2–60 mM | 15 mM |
| L-Arginine HCl | 2–60 mM | 10 mM |

The buffer medium is preferably administered in an amount ranging from about 10 cc to about 300 cc. For example, the transplant site may be prepared by injecting about 120 cc of the buffer medium prior to implanting the transplant. Following implantation, an additional amount of the buffer medium may be administered to the transplant site. For example, the implant may be followed by another injection of about 120 cc of the buffer medium. Further injections of about 120 cc of the buffer may be made daily for the next one to seven days. The nitric oxide inhibitors within the buffer medium inhibit the attraction and activation of immune cells in the area of the implant, thereby further aiding the process of permissive acceptance of the transplanted tissue.

The following examples are offered by way of illustration and not by way of limitation.

EXPERIMENTAL

Matrix Preparation

Place 835 ml of Medium 199 into a beaker. While stirring, heat the solution to 50° C. Using a syringe, add 20 ml of albumin to the stirred solution. Pipette 63.28 $\mu$l of L-cysteine, 1 ml of L-glutamine and 200 $\mu$l of aminoguanidine into the stirred beaker. Add the following gamma irradiated dry raw materials: 120 grams of denatured collagen, 50 grams of dextran, and 0.1 grams of intact collagen. Use a glass stirring rod to aid mixing of the dry materials into solution. Pipette 8 ml of EDTA into the solution. Pipette 5 ml of L-glutamic acid, 5 ml of L-lysine acetate, and 5 ml of L-arginine HCl into the stirred beaker. Note that the solution will turn yellow. Use 10% NaOH to adjust the pH of the matrix solution to a final pH of 7.40±0.05.

Cells may be embedded in the matrix of the present invention using the following procedure. Aspirate the supernatant from centrifuged cell pellets. Add a volume of cell culture medium and matrix to the cell pellets. Add a volume of matrix approximately equal to about 4 times the pellet volume. Add a volume of cell culture medium to the cell pellets equaling approximately 0.05 times the matrix volume added. Store the encapsulated cells at refrigerated temperatures if not using immediately.

EXAMPLE 1

Figure 1:
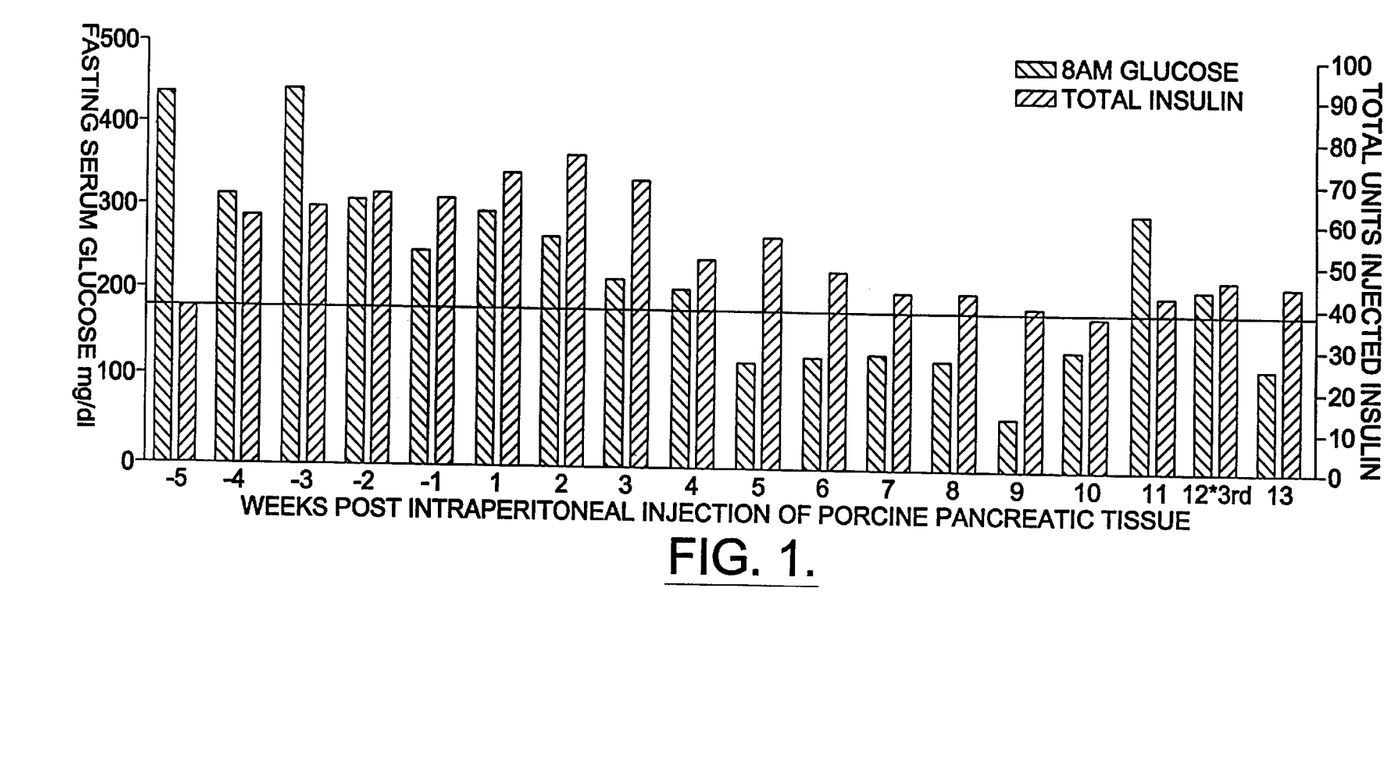
FIG. 1 is a bar chart illustrating the fasting glucose levels and total insulin dose for a dog after an intraperitoneal injection of porcine pancreatic tissue.

A pancreatectomized diabetic dog was injected intraperitoneally with a porcine pancreatic tissue/matrix transplant after five weeks of diabetes. FIG. 1 illustrates the fasting AM glucose levels and total supplemented insulin for the dog over an 18 week period, including the five weeks prior to injection. A second intraperitoneal injection was made on last day of week 3. The second injection was preceded by an injection of the buffer medium described above and followed by daily injections of the buffer medium for three days following implantation. At week 6, insulin injections were dropped to once a day, instead of twice a day. At week 7, regular insulin injections ceased and only ultralente insulin was administered daily. A third peritoneal injection was administered on the last day of week 12 with the buffer medium administered to the transplant site prior to injection. The target glucose level is 180 mg/dl or lower. As shown, the injections reduced the glucose level of the dog and reduced the amount of insulin required to maintain the target glucose level.

EXAMPLE 2

Figure 2:
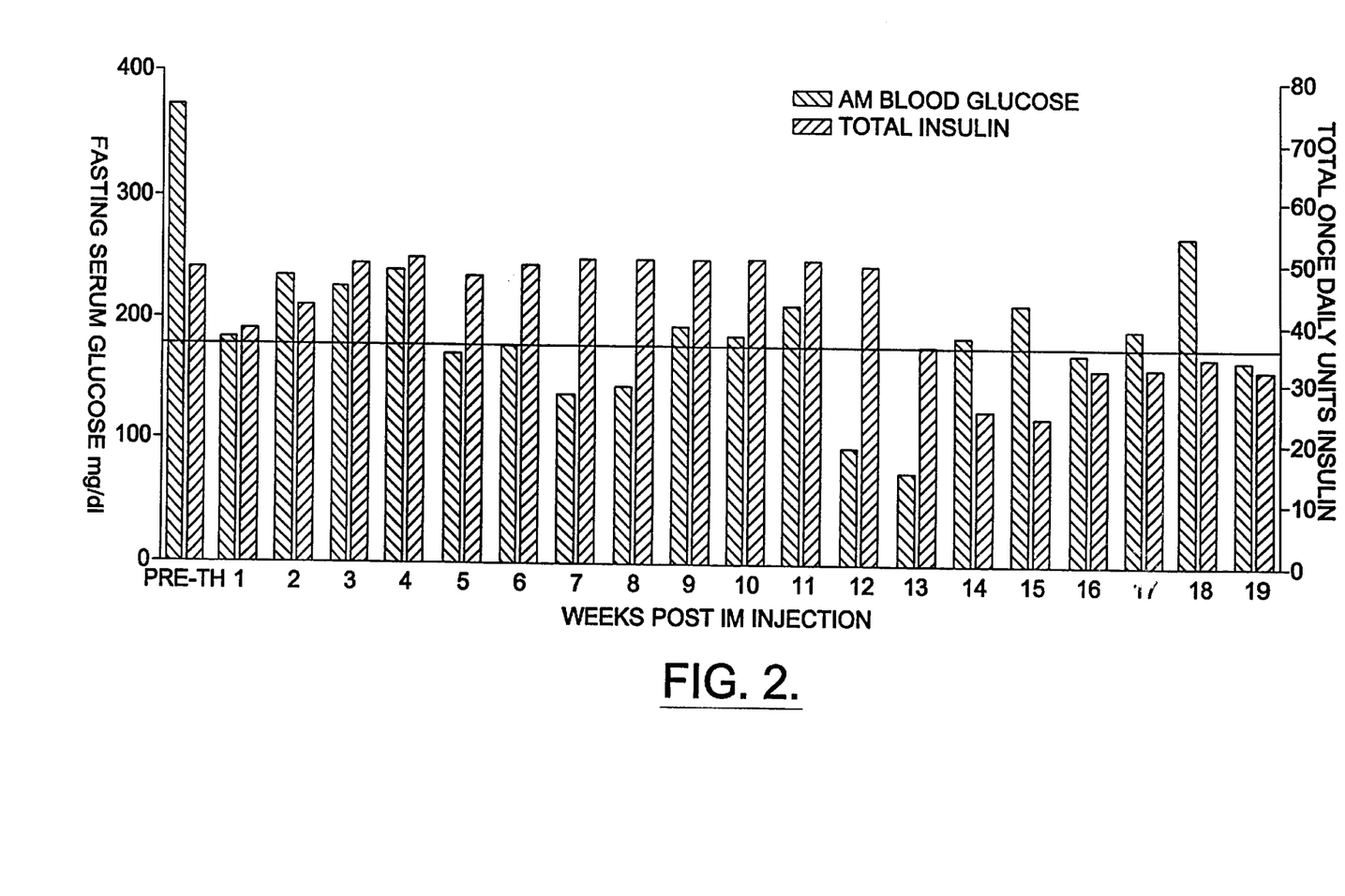
FIG. 2 is a bar chart illustrating the fasting glucose levels and total insulin dose for a dog after intramuscular injection of porcine pancreatic tissue.

A pancreatectomized diabetic dog was injected intramuscularly with a porcine pancreatic tissue/matrix transplant. FIG. 2 illustrates the fasting AM glucose levels and total supplemented insulin for the dog over a 19 week period following the injection. As shown, the amount of insulin required to maintain the target glucose value (180 mg/dl or less) decreased after the injection and the average glucose level of the dog decreased.

EXAMPLE 3

Two canine subjects were pancreatectomized within two weeks of each other and were treated with injections of mixtures of Ultralente and Regular insulin twice daily. Both animals were fed identical amounts of food with Viokase added to replace pancreatic digestive enzymes. Blood glucose values were determined in the morning and late afternoon, and exogenous insulin requirements were based on these values.

Figure 3:
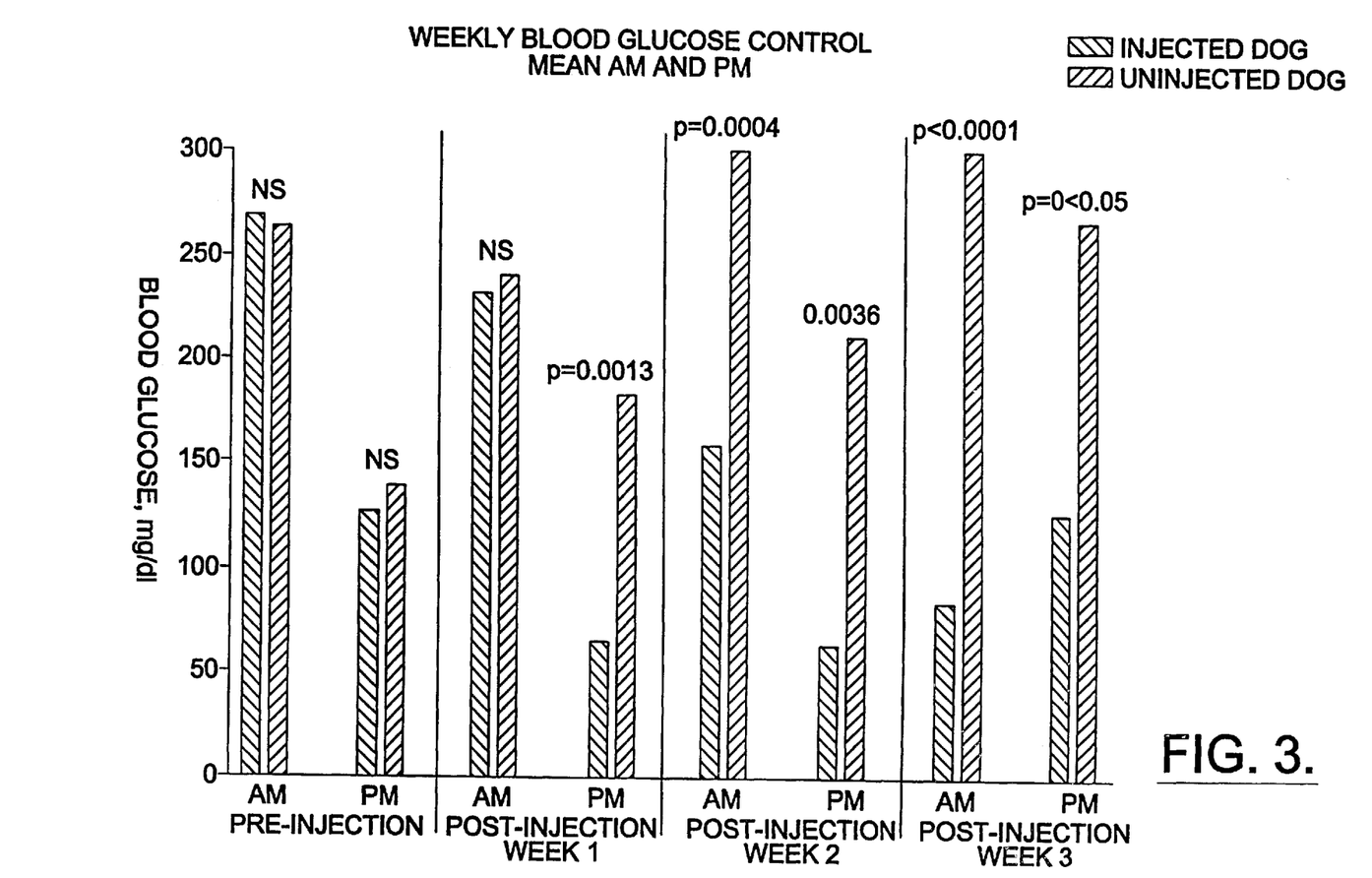
FIG. 3 is a bar chart showing the relationship between the blood glucose levels of two dogs.

For four weeks prior to one of the dogs being injected with 8 cc of one volume unpurified pancreatic tissue per four volumes matrix, the two dogs had statistically equivalent blood glucose determinations, and received the same dose of insulin twice daily. The blood glucose levels of a dog that was not injected (darkly shaded line) and a dog that was ultimately injected intramuscularly on Day 0 (lightly shaded line) are shown in FIG. 3. The daily AM and PM blood glucose determinations are shown beginning one week prior to injection, and out for a total of three weeks (22 days).

FIG. 3 demonstrates that there was no statistical difference in the AM or PM blood glucose determinations during the week prior to one dog receiving the porcine tissue injection. Beginning the day of injection, the injected dog had a statistically significant decrease in the PM blood glucose on the same insulin dose as the uninjected dog. There was no statistically significant difference in the AM blood glucose during the first week after injection, probably reflecting the increased insulin resistance that mammals experience in the morning due to the effects of counter regulatory hormones such as cortisol and growth hormone. Type I diabetics generally require twice as much insulin in the AM to cover the same ingestion of carbohydrates as they require pre-supper because of this AM "cortisol" effect.

Beginning seven days after the injection, blood glucose levels in the injected dog clearly separated from those of the uninjected animal. Both animals had their insulin decreased 15% beginning week two. The injected dog's glucose continued to normalize, while the uninjected dog's blood glucose rose as expected. The injected animal continued to have statistically significant decreased blood glucose compared to the uninjected animal over the three week period. At that point, we separated the animals' insulin dose so that the uninjected dog could be better controlled.

EXAMPLE 4

The uninjected animal in Example 3 was injected with unpurified porcine pancreatic tissue embedded in the matrix of the present invention to further protect the cells from immune recognition. Approximately 8 cc of this material was injected intramuscularly into the previously uninjected dog.

Beginning that evening, the dog's blood glucose fell, and the total insulin dose was cut 33%. The dog went at least seven days with the change in daily mean blood glucose and daily mean insulin dose shown below:

TABLE 3

|  | Mean daily Blood Glucose | Mean total daily insulin dose |
| --- | --- | --- |
| Seven days prior to injection | 180 mg % | 64 units |
| Seven days post injection | 101 mg % | 43 units |

These data demonstrate that the injected porcine tissue has the effect of more than 20 units of exogenously administered insulin, since the average blood glucose has fallen nearly 40% and normalized on 20 units less insulin. The total daily insulin released in the average human subject is approximately 0.25 units/kg body weight, or 20 units per day in an 80 kg man. These data do not necessarily reflect 20 units of insulin production, since the pulsatile release of the pancreatic tissue probably increases the animal's insulin sensitivity.

These data clearly show the ability of unpurified porcine pancreatic tissue to function without the use of immunosuppression. Based on the above figures, isolated cells from three pancreases could treat 30–50 patients.

Many modifications and other embodiments of the invention will come to mind to one skilled in the art to which this invention pertains having the benefit of the teachings presented in the foregoing descriptions and associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of obscuring immune recognition of a transplant by a host mammal, comprising:
   providing a transplant suitable for implantation in a mammal;
   providing a hydrogel matrix, the matrix comprising
   gelatin,
   dextran,
   at least one nitric oxide inhibitor, and
   an effective amount of polar amino acids, the polar amino acids selected from the group consisting of arginine, lysine, histidine, glutamic acid, and aspartic acid; and encapsulating the transplant within the hydrogel matrix;

said effective amount of polar amino acids being the amount necessary to increase the rigidity of the matrix and allow direct injection of the matrix with the transplant encapsulated therein into a host mammal without the need for further immunosuppression.

2. A method according to claim 1, further comprising implanting the transplant into a transplant site in a mammal.

3. A method according to claim 2, wherein said implanting step comprises injecting the transplant into the mammal.

4. A method according to claim 2, wherein said implanting step comprises implanting the transplant intramuscularly, subcutaneously, intra-organ, intravascularly, or intraperitoneally.

5. A method according to claim 1, wherein the transplant comprises tissue, the tissue comprising cells having cell surface proteins.

6. A method according to claim 5, wherein said encapsulating step comprises encapsulating the tissue within the hydrogel matrix such that the matrix binds to the cell surface proteins of the tissue.

7. A method according to claim 6, wherein the transplant further comprises a carrier device, the carrier device housing the encapsulated tissue.

8. A method according to claim 5, wherein the tissue comprises cells selected from the group consisting of lung cells, liver cells, kidney cells, thymus cells, thyroid cells, heart cells, brain cells, pancreatic islet cells, pancreatic acinar cells and mixtures thereof.

9. A method according to claim 5, wherein the tissue is derived from a different species than the host mammal.

10. A method according to claim 1, wherein the gelatin comprises denatured collagen fragments, the collagen fragments providing exposed polar groups.

11. A method according to claim 10, wherein the gelatin comprises about 0.01 to about 40 mM of denatured collagen.

12. A method according to claim 1, wherein the effective amount of polar amino acids comprises about 3 to about 150 mM of polar amino acids.

13. A method according to claim 12, wherein the effective amount of polar amino acids comprises about 10 to about 65 mM of polar amino acids.

14. A method according to claim 1, wherein the at least one nitric oxide inhibitor is selected from the group consisting of cysteine, L-arginine analogues, cystine, and heparin.

15. A method according to claim 1, wherein the at least one nitric oxide inhibitor comprises about 5 to about 500 $\mu$M of L-cysteine and about 5 to about 500 $\mu$M of an L-arginine analogue.

16. A method according to claim 15, wherein the L-arginine analogue is aminoguanidine.

17. A method according to claim 1, wherein the effective amount of polar amino acids comprises:

about 2 to about 60 mM of L-glutarnic acid;

about 0.5 to about 30 mM of L-lysine; and about 1 to about 40 mM of Larginine.

18. A method according to claim 17, wherein the effective amount of polar amino acids comprises:

about 5 to about 40 mM of L-glutamic acid;

about 1 to about 15 mM of L-lysine; and about 1 to about 30 mM of L-arginine.

19. A method according to claim 1, wherein the matrix further comprises a superoxide inhibitor.

20. A method according to claim 19, wherein the superoxide inhibitor is EDTA.

21. A method according to claim 2, further comprising applying a buffer medium to the transplant site prior to implanting the transplant, the buffer medium comprising at least one nitric oxide inhibitor.

22. A method according to claim 21, wherein the at least one nitric oxide inhibitor of the buffer medium comprises about 50 to about 300 $\mu$M of L-cysteine and about 15 to about 250 $\mu$M of an L-arginine analogue.

23. A method according to claim 21, wherein said applying step comprises applying about 10 to about 300 cc. of the buffer medium to the transplant site.

24. A method according to claim 21, further comprising applying a buffer medium to the transplant site after implanting the transplant, the buffer medium comprising at least one nitric oxide inhibitor.

25. A method according to claim 24, wherein the at least one nitric oxide inhibitor of the buffer medium comprises about 50 to about 300 $\mu$M of L-cysteine and about 15 to about 250 $\mu$M of an L-arginine analogue.

26. A method of obscuring immune recognition of a transplant by a host mammal, comprising:

providing tissue suitable for use in a transplant, the tissue comprising cells having cell surface proteins;

providing a hydrogel matrix, the matrix comprising
gelatin,
dextran,
at least one nitric oxide inhibitor, and
an effective amount of polar amino acids, the polar amino acids selected from the group consisting of arginine, lysine, histidine, glutarnic acid, and aspartic acid;

encapsulating the tissue within the hydrogel matrix to form an encapsulated transplant, the matrix binding to the cell surface proteins of the tissue;

applying a first amount of a buffer medium to a transplant site of a mammal, the buffer medium comprising at least one nitric oxide inhibitor;

implanting the encapsulated transplant into the transplant site after application of the first amount of the buffer medium; and applying a second amount of the buffer medium to the transplant site after implanting the encapsulated transplant;

said effective amount of polar amino acids being the amount necessary to increase the rigidity of the matrix and allow direct injection of the matrix with the transplant encapsulated therein into a host mammal without the need for further immunosuppression.

27. A method according to claim 26, wherein the at least one nitric oxide inhibitor of the buffer medium comprises about 50 to about 300 $\mu$M of L-cysteine and about 15 to about 250 $\mu$M of an L-arginine analogue.

28. A method according to claim 26, wherein the buffer medium further comprises a superoxide inhibitor.

29. A method according to claim 26, further comprising the step of applying the buffer medium to the transplant site about once a day for about one to about seven days following said implanting.

* * * * *

UNITED STATES PATENT AND TRADEMARK OFFICE
CERTIFICATE OF CORRECTION

PATENT NO.    : 6,352,707 B1
DATED         : March 5, 2002
INVENTOR(S)   : Usala It is certified that error appears in the above-identified patent and that said Letters Patent is hereby corrected as shown below:

Title page,
Item [56], References Cited, FOREIGN PATENT DOCUMENTS, "2/1988" should read -- 2/1998 --.
OTHER PUBLICATIONS, "Angiogensis" should read -- Angiogenesis --.

Column 5, Table 1,
Line 37, "t0" should read -- to --.

Column 8, Table 2,
Line 22, "Arnphotericin B" should read -- Amphotericin B --.

Column 11,
Line 57, "glutarnic" should read -- glutamic --;
Line 60, "Larginine" should read -- L-arginine --.

Column 12,
Line 34, "glutarnic" should read -- glutamic --.

Signed and Sealed this

Third Day of September, 2002

Attest:

Attesting Officer

JAMES E. ROGAN
Director of the United States Patent and Trademark Office